(12) United States Patent
Zhang et al.

(10) Patent No.: US 11,439,661 B2
(45) Date of Patent: Sep. 13, 2022

(54) OPHTHALMIC COMPOSITIONS

(71) Applicant: ALCON INC., Fribourg (CH)

(72) Inventors: Steve Yun Zhang, Sugar Hill, GA (US); Richard Charles Breitkopf, Dunwoody, GA (US); Daqing Wu, Suwanee, GA (US); Junhao Ge, Johns Creek, GA (US); Maria F. Gubitosi Raspino, Lilburn, GA (US); Augustine Twum Kumi, Grayson, GA (US); Wei Liang, Johns Creek, GA (US)

(73) Assignee: Alcon Inc., Fribourg (CH)

(*) Notice: Subject to any disclaimer, the term of this patent is extended or adjusted under 35 U.S.C. 154(b) by 117 days.

(21) Appl. No.: 16/911,833

(22) Filed: Jun. 25, 2020

(65) Prior Publication Data

US 2020/0405747 A1 Dec. 31, 2020

Related U.S. Application Data

(60) Provisional application No. 62/868,220, filed on Jun. 28, 2019.

(51) Int. Cl.
| | | |
|---|---|---|
| A61K 31/80 | (2006.01) | |
| A61P 27/04 | (2006.01) | |
| A61K 31/015 | (2006.01) | |
| A61K 31/07 | (2006.01) | |
| A61K 31/122 | (2006.01) | |
| A61K 31/202 | (2006.01) | |
| A61K 31/355 | (2006.01) | |
| A61K 31/593 | (2006.01) | |
| A61K 31/736 | (2006.01) | |
| A61K 45/06 | (2006.01) | |
| A61K 47/10 | (2017.01) | |
| A61K 47/26 | (2006.01) | |
| A61K 47/34 | (2017.01) | |

(52) U.S. Cl.
CPC ............ *A61K 31/80* (2013.01); *A61K 31/015* (2013.01); *A61K 31/07* (2013.01); *A61K 31/122* (2013.01); *A61K 31/202* (2013.01); *A61K 31/355* (2013.01); *A61K 31/593* (2013.01); *A61K 31/736* (2013.01); *A61K 45/06* (2013.01); *A61K 47/10* (2013.01); *A61K 47/26* (2013.01); *A61K 47/34* (2013.01); *A61P 27/04* (2018.01)

(58) Field of Classification Search
CPC ...... A61K 31/80; A61K 31/015; A61K 31/07; A61P 27/04

See application file for complete search history.

(56) References Cited

U.S. PATENT DOCUMENTS

| | | | | |
|---|---|---|---|---|
| 10,828,320 | B2* | 11/2020 | Davis | A61K 47/32 |
| 10,962,803 | B2* | 3/2021 | Zhang | C08J 7/0427 |
| 2009/0270345 | A1 | 10/2009 | Ketelson | |
| 2011/0275593 | A1 | 11/2011 | Ketelson | |
| 2012/0026457 | A1 | 2/2012 | Qiu | |
| 2013/0296264 | A1 | 11/2013 | Davis | |

FOREIGN PATENT DOCUMENTS

| | | |
|---|---|---|
| EP | 3395348 A4 | 10/2018 |
| WO | 2009064983 A1 | 5/2009 |
| WO | 2016032940 A1 | 3/2016 |

* cited by examiner

*Primary Examiner* — Kevin E Weddington

(74) *Attorney, Agent, or Firm* — Sheng-Hsin Hu

(57) ABSTRACT

The invention is generally related to topical ophthalmic compositions comprising: from about 0.05 w/v % to about 5 w/v % of galactomannan polymer; a cis-diol and about 0.5 w/v % to about 10 w/v % of a hydrophilic copolymer which comprises (a) arylborono-containing repeating units each having a boronic acid, (b) repeating units of at least one phosphorylcholine-containing vinylic monomer, and (c) acrylic monomeric units of at least one acrylic monomer having 3 to 16 carbon atoms, the ophthalmic composition is substantially free of a borate for improving lubrication, hydration and drug delivery property.

19 Claims, No Drawings

OPHTHALMIC COMPOSITIONS

This invention relates to topical ophthalmic compositions containing a galactomannan and a hydrophilic copolymer comprises (a) arylborono-containing repeating units each having a boronic acid, (b) repeating units of at least one phosphorylcholine-containing vinylic monomer, and (c) acrylic monomeric units of at least one acrylic monomer for improving lubrication, hydration and drug delivery property.

BACKGROUND

Integrity of the tear film is essential for ocular surface homeostasis and functioning. Dry eye disease is a multifactorial condition characterized by tear film instability, and results in ocular discomfort and visual disturbance, severely impacting patient's quality of life. The outermost lipid layer of the tear film, formed by the meibum, helps to maintain tear film stability by reducing the rate of tear evaporation. Alteration in the tear lipid layer due to impaired quality or quantity of the meibum, is one of the most common cause of evaporative dry eye disease. Topically administered artificial tear substitutes/lubricant eye drops are the mainstay in the management of all types of dry eye disease and alleviate the symptoms and signs in patients with dry eye.

Chronic dry eye can lead to desiccation and damage of ocular surface tissues and disrupted epithelial cell barrier function. Instillation of lubricating artificial tears that replenish moisture and decrease friction is a primary approach to dry eye management. Artificial tear compositions comprise compounds that lubricate and protect the ocular surface. In the context of dry eye disorders, artificial tear compositions can prevent symptoms such as pain and discomfort and can prevent bioadhesion and tissue damage induced by friction. A large number of potential compounds are available that are useful as lubricants and ocular surface protectants. For example, certain marketed artificial tear products contain natural polymers such as galactomannans. Other lubricants and ocular surface protectants include, for example, carboxymethylcellulose, glucomannan, and hydroxypropylmethylcellulose. Though existing artificial tear compositions have met with some success, problems in the treatment of dry eye nevertheless remain. The use of tear substitutes, while temporarily effective, generally requires repeated application over the course of a patient's waking hours. It is not uncommon for a patient to have to apply artificial tear solution ten to twenty times over the course of the day. Such an undertaking is not only cumbersome and time consuming, but is also potentially very expensive, often leading to patient compliance issues.

There is still a need to develop improved ophthalmic compositions, which can provide better lubricity, can suppress moisture evaporation from contact lens an eye can, have a higher efficiency in coating the ocular surface, and/or can integrate better with the existing tear film to provide protection.

SUMMARY

The present invention is directed to topical ophthalmic compositions comprising: from about 0.05 w/v % to about 5 w/v % of galactomannan polymer; a cis-diol and about 0.5 w/v % to about 10 w/v % of a hydrophilic copolymer which comprises (a) arylborono-containing repeating units each having a boronic acid, (b) repeating units of at least one phosphorylcholine-containing vinylic monomer, and (c) acrylic monomeric units of at least one acrylic monomer having 3 to 16 carbon atoms, the ophthalmic composition is substantially free of a borate. The present invention is also directed to methods of using these compositions to treat various ophthalmic disorders including dry eye, glaucoma, ocular hypertension, infection, allergy and inflammation.

DETAILED DESCRIPTION

Unless defined otherwise, all technical and scientific terms used herein have the same meaning as commonly understood by one of ordinary skill in the art to which this invention belongs. Generally, the nomenclature used herein and the laboratory procedures are well known and commonly employed in the art. Conventional methods are used for these procedures, such as those provided in the art and various general references. Where a term is provided in the singular, the inventors also contemplate the plural of that term. The nomenclature used herein and the laboratory procedures described below are those well-known and commonly employed in the art.

"About" as used herein means that a number referred to as "about" comprises the recited number plus or minus 1-10% of that recited number.

"Optional" or "optionally" means that the subsequently described event or circumstance can or cannot occur, and that the description includes instances where the event or circumstance occurs and instances where it does not.

The term "ethylenically unsaturated group" is employed herein in a broad sense and is intended to encompass any groups containing at least one >C=C< group. Exemplary ethylenically unsaturated groups include without limitation (meth)acryloyl

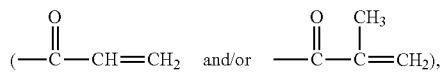

allyl, vinyl

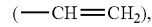

1-methylethenyl

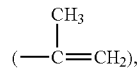

styrenyl, or the likes.

The term "(meth)acrylamide" refers to methacrylamide and/or acrylamide.

The term "(meth)acrylate" refers to methacrylate and/or acrylate.

An "acrylic monomer" refers to a vinylic monomer having one sole (meth)acryloyl group.

As used in this application, the term "vinylic crosslinker" refers to a compound having at least two ethylenically unsaturated groups. A "vinylic crosslinking agent" refers to a vinylic crosslinker having a molecular weight of about 700 Daltons or less.

As used in this application, the term "polymer" means a material formed by polymerizing/crosslinking one or more monomers or macromers or prepolymers.

As used in this application, the term "molecular weight" of a polymeric material (including monomeric or macromeric materials) refers to the weight-average molecular weight unless otherwise specifically noted or unless testing conditions indicate otherwise.

The term "alkyl" refers to a monovalent radical obtained by removing a hydrogen atom from a linear or branched alkane compound. An alkyl group (radical) forms one bond with one other group in an organic compound.

The term "alkylene divalent radical" or "alkylene diradical" or "alkyl diradical" interchangeably refers to a divalent radical obtained by removing one hydrogen atom from an alkyl. An alkylene divalent group forms two bonds with other groups in an organic compound.

The term "alkyl triradical" refers to a trivalent radical obtained by removing two hydrogen atoms from an alkyl. A alkyl triradical forms three bonds with other groups in an organic compound.

The term "alkoxy" or "alkoxyl" refers to a monovalent radical obtained by removing the hydrogen atom from the hydroxyl group of a linear or branched alkyl alcohol. An alkoxy group (radical) forms one bond with one other group in an organic compound.

In this application, the term "substituted" in reference to an alkyl diradical or an alkyl radical means that the alkyl diradical or the alkyl radical comprises at least one substituent which replaces one hydrogen atom of the alkyl diradical or the alkyl radical and is selected from the group consisting of hydroxy (—OH), carboxy (—COOH), —NH$_2$, sulfhydryl (—SH), C$_1$-C$_4$ alkyl, C$_1$-C$_4$ alkoxy, C$_1$-C$_4$ alkylthio (alkyl sulfide), C$_1$-C$_4$ acylamino, C$_1$-C$_4$ alkylamino, di-C$_1$-C$_4$alkylamino, halogen atom (Br or Cl), and combinations thereof.

In this application, an "arylborono-containing vinylic monomer" refers to a vinylic monomer which comprises one sole arylborono group linked to its sole ethylenically unsaturated group through one linkage.

In this application, an "arylborono" group refers to a substituted phenyl group having one boronic acid group (i.e., —B(OH)$_2$) and optionally one or more other groups as substituents each of which replaces one hydrogen atom of the phenyl group.

As used in this application, the term "phosphorylcholine" refers to a monovalent zwitterionic group of

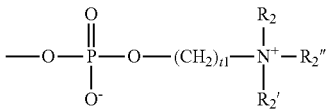

in which t1 is an integer of 1 to 5 and R$_2$, R$_2$' and R$_2$" independently of one another are C$_1$-C$_8$ alkyl or C$_1$-C$_8$ hydroxyalkyl.

An "initiator" refers to a chemical that can initiate free radical crosslinking/polymerizing reaction.

In general, the invention is directed to an ophthalmic composition comprising: from about 0.05 w/v % to about 5 w/v % of galactomannan polymer; a cis-diol and about 0.5 w/v % to about 10 w/v % of a hydrophilic copolymer which comprises (a) arylborono-containing repeating units each having a boronic acid, (b) repeating units of at least one phosphorylcholine-containing vinylic monomer, and (c) acrylic monomeric units of at least one acrylic monomer having 3 to 16 carbon atoms, the composition is substantially free of a borate. The present invention is also directed to methods of using these compositions to treat various ophthalmic disorders including dry eye, glaucoma, ocular hypertension, infection, allergy and inflammation.

Commercial available ophthalmic compositions, for example, Systane family products comprise guar and boric acid. Natural guar galactomannan is a water-soluble polysaccharide, which results in high viscosity even when low concentrations are dissolved in aqueous solutions. This high viscosity is in part due to its high molecular weight and the intermolecular associations occurring in the presence of borate ions. Natural guar can be treated with propylene oxide to form a more hydrophobic, surface active hydroxypropyl guar (HP-guar). Once exposed to the pH of the ocular tears and surface, approximately 7.5 pH, the HP-guar in Systane forms a "soft" gel with increased viscosity and bioadhesive properties that are designed to promote retention of the two demulcents to protect the ocular surface microenvironment.

The present invention is to improve the commercial available ophthalmic compositions by providing a hydrophilic copolymer which comprises (a) arylborono-containing repeating units each having a boronic acid, (b) repeating units of at least one phosphorylcholine-containing vinylic monomer, and (c) acrylic monomeric units of at least one acrylic monomer having 3 to 16 carbon atoms for improving lubrication, hydration and drug delivery property. In addition, the ophthalmic composition is substantially free of a borate.

Boronic acids containing polymer has the ability to form reversible covalent complexes with 1,2- or 1,3-diols. In aqueous systems, boronic acids exist in equilibrium between an undissociated neutral trigonal form (1) and a dissociated anionic tetrahedral form (2) (Scheme 1). In the presence of 1,2- or 1,3-diols, cyclic boronate esters formed by reaction of the neutral boronic acid with a diol are generally considered hydrolytically unstable. On the other hand, reaction of the anionic boronate anion (2) with a diol leads to stable boronate esters (3). Therefore, the net effect of adding reactive diols to boronic acids (1) in aqueous media is a shift in equilibrium to the anionic forms (2 and 3). As a result, guar galactomannan containing 1,2- and/or 1,3-diols can form high viscosity even when low concentrations are dissolved in aqueous solutions due to its high molecular weight and the intermolecular associations occurring in the presence of boronic acids, just like in the presnece of borate ions. Therefore, according to the present invention, the ophthalmic composition is substantially free of a borate. Substantially free of a borate refers to be less than 0.1% W/V borate, preferably less than 0.05% W/V borate, more preferably less than 0.02% W/V borate.

It is believed that boronic acids containing polymer has a strong affinity for mucin due to its ability to complex with 1, 2-cis-diols. In addition, boronic acids containing polymer provides an ocular delivery property. For example, Phenylboronic acid (PBA) is a synthetic molecule that has been extensively used in glucose sensing and insulin delivery systems due to its ability to form high-affinity complexes with 1, 2-cis-diols. This affinity between boronic acids and diols has also been utilized in other mucoadhesive drug delivery systems such as vaginal delivery of interferon nasal delivery of insulin, and ocular delivery of cyclosporine A (CycA).

It is believed that phosphorylcholine-containing polymer increases cell compatibility and enhance lubricity because of the biomembrane-like structure of the organic phosphate groups. In addition, phosphorylcholine-containing polymer suppresses nonspecific protein adsorption, increases cell compatibility, enhances the anti-biofouling properties and biocompatibility and Improve water holding capability.

It is further believed that the hydrophilic copolymer which comprises (a) arylborono-containing repeating units each having a boronic acid, (b) repeating units of at least one phosphorylcholine-containing vinylic monomer, and (c) acrylic monomeric units of at least one acrylic monomer having 3 to 16 carbon atoms is a mucoadhesive polymer that would stick to the immobilized mucin layer of the tear film to enhance and retain wetting.

Scheme I

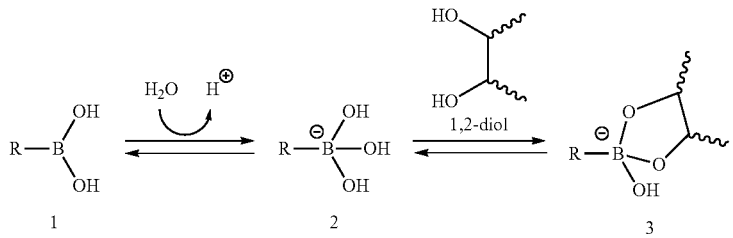

In accordance with the invention, any galactomannan polymers can be used in the present invention. As used herein, the term "galactomannan" refers to polysaccharides derived from the above natural gums or similar natural or synthetic gums containing mannose or galactose moieties, or both groups, as the main structural components. Preferred galactomannan polymers are made up of linear chains of (1-4)-β-D-mannopyranosyl units with α-D-galactopyranosyl units attached by (1-6) linkages. With the preferred galactomannan polymers, the ratio of D-galactose to D-mannose varies, but generally will be from about 1:2 to 1:4. Galactomannan polymers having a D-galactose:D-mannose ratio of about 1:2 are most preferred. Additionally, other chemically modified variations of the polysaccharides are also included in the "galactomannan polymer" definition, so long as they still have 1,3-diol moieties. For example, hydroxyethyl, hydroxypropyl and carboxymethylhydroxypropyl substitutions may be made to the galactomannan polymers. Non-ionic variations to the galactomannan polymers, such as those containing alkoxy and alkyl ($C_1$-$C_6$) groups are particularly preferred when a soft gel is desired (e.g., hydroxylpropyl substitutions). Substitutions in the non-cis hydroxyl positions are most preferred. An example of non-ionic substitution of a galactomannan polymer of the present invention is hydroxypropyl guar, with a molar substitution of about 0.4. Anionic substitutions may also be made to the galactomannan polymers. Anionic substitution is particularly preferred when strongly responsive gels are desired.

Galactomannan polymers may be obtained from numerous sources. Such sources include guar gum, locust bean gum and Lara gum, as further described below. Additionally, the galactomannans may also be obtained by classical synthetic routes or may be obtained by chemical modification of naturally occurring galactomannans.

Guar gum is the ground endosperm of *Cyamopisis tetragonolobus* (L.) Taub. The water soluble fraction (85%) is called "guaran" (molecular weight of 220,000), which consists of linear chains of (1-4)-β-D mannopyranosyl units with α-D-galactopyranosyl units attached by (1-6) linkages. The ratio of D-galactose to D-mannose in guaran is about 1:2. The gum has been cultivated in Asia for centuries and is primarily used in food and personal care products for its thickening property. It has five to eight times the thickening power of starch. Its derivatives, such as those containing hydroxypropyl or hydroxypropyltrimonium chloride substitutions, have been commercially available for over a decade. Guar gum may be obtained, for example, from Rhone-Polulenc (Cranbury, N.J.), Hercules, Inc. (Wilmington, Del.) and TIC Gum, Inc. (Belcamp, Md.).

Locust bean gum or carob bean gum is the refined endosperm of the seed of the carob tree, *ceratonia siliqua*. The ratio of galactose to mannose for this type of gum is about 1:4. Cultivation of the carob tree is old and well known in the art. This type of gum is commercially available and may be obtained from TIC Gum, Inc. (Bekamp, Md.) and Rhone-Polulenc (Cranbury, N.J.).

Tara gum is derived from the refined seed gum of the tara tree. The ratio of galactose to mannose is about 1:3. Tara gum is not produced in the United States commercially, but the gum may be obtained from various sources outside the United States.

In order to limit the extent of cross-linking to provide a softer gel characteristic, chemically modified galactomannans such as hydroxypropyl guar may be utilized. Modified galactomannans of various degree of substitution are commercially available from Rhone-Poulenc (Cranbury, N.J.). Hydroxypropyl guar with low molar substitution (e.g., less than 0.6) is particularly preferred.

In accordance with the invention, galactomannan polymer is typically present in an ophthalmic composition of the present invention at a concentration of from about 0.05 to about 5 w/v %, preferably from about 0.5 to about 2.0 w/v %, more preferably from about 0.2 to about 1.5 w/v %, and most preferably from about 0.25 to about 1.0 w/v %. Preferred galactomannan polymers of the present invention are guar and hydroxypropyl guar.

According to the invention, the hydrophilic copolymer comprises (a) from about 1% to about 20% by mole (preferably from about 1% to about 20% by mole, more preferably from about 2% to about 15% by mole) of arylborono-containing repeating units each having a boronic acid, (b) from about 60% to about 98% by mole (preferably from about 60% to about 97% by mole, more preferably from about 70% to about 95% by mole) of repeating units of at least one phosphorylcholine-containing vinylic monomer, and (c) from about 1% by mole to about 20% by mole (preferably from about 2% to about 20% by mole, more preferably from about 3% to about 15% by mole) of acrylic monomeric units of at least one acrylic monomer having 3 to 16 (preferably 3 to 14, more preferably 3 to 12, even more preferably 3 to 10) carbon atoms, provided that the sum of the mole percentages of components (a), (b) and (c) and other components not listed above is 100%.

In accordance with the invention, the mole percentages of each type of repeating units (i.e., monomeric units) of a hydrophilic copolymer can be determined based on the mole percentage of a vinylic monomer, from which this type of repeating units are derived, in a polymerizable composition for forming the hydrophilic copolymer.

In accordance with the invention, each type of arylborono-containing repeating units can be derived directly from an arylborono-containing vinylic monomer, preferably from an arylborono-containing vinylic monomer of formula (I)

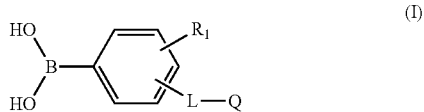

in which: $R_1$ is H, $NO_2$, F, Cl, or $CF_3$; Q is a monovalent radical of

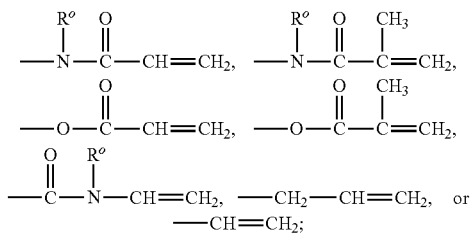

L is a direct bond, a $C_1$-$C_4$ alkylene divalent radical, a divalent radical of

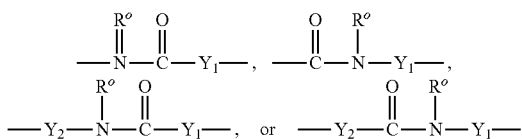

in which $Y_1$ is CH(OH) or a $C_1$-$C_4$ alkylene divalent radical, $Y_2$ is a $C_1$-$C_4$ alkylene divalent radical, and $R^o$ is H or a $C_1$-$C_4$ alkyl.

Examples of arylborono-containing vinylic monomers of formula (I) include without limitation 3-vinylphenylboronic acid, 4-vinylboronic acid, 3-(meth)acrylamidophenylboronic acid, 4-(meth)acrylamidophenylboronic acid, a reaction production of an amino-containing phenylboronic acid derivative with (meth)acrylic acid halide, a reaction product of an amino-containing phenylboronic acid derivative with a carboxy-containing vinylic monomer in the presence of a carbodiimide (e.g., 1-ethyl-3-(3-dimethylaminopropyl) carbodiimide (EDC), N,N'-dicyclohexylcarbodiimide (DCC), 1-cylcohexyl-3-(2-morpholinoethyl)carbodiimide, diisopropyl carbodiimide, or mixtures thereof) and N-hydroxysuccinimide, a reaction production of a carboxy-containing phenylboronic acid derivative with an amino-containing vinylic monomer in the presence of a carbodiimide (e.g., 1-ethyl-3-(3-dimethylaminopropyl) carbodiimide (EDC), N,N'-dicyclohexylcarbodiimide (DCC), 1-cylcohexyl-3-(2-morpholinoethyl)carbodiimide, diisopropyl carbodiimide, or mixtures thereof) and N-hydroxysuccinimide, and combinations thereof.

Examples of phosphorylcholine-containing vinylic monomers include without limitation (meth)acryloyloxyethyl phosphorylcholine (aka, MPG, or 2-((meth)acryloyloxy) ethyl-2'-(trimethylammonio)ethylphosphate), (meth)acryloyloxypropyl phosphorylcholine (aka, 3-((meth)acryloyloxy)propyl-2'-(trimethylammonio)ethylphosphate), 4-((meth)acryloyloxy)butyl-2'-(trimethylammonio)ethylphosphate, 2-[(meth)acryloylamino]ethyl-2'-(trimethylammonio)-ethylphosphate, 3-[(meth)acryloylamino]propyl-2'-(trimethylammonio)ethylphosphate, 4-[(meth)acryloylamino]butyl-2'-(trimethylammonio)ethylphosphate, 5-((meth)acryloyloxy)pentyl-2'-(trimethylammonio)ethyl phosphate, 6-((meth)acryloyloxy)hexyl-2'-(trimethylammonio)-ethylphosphate, 2-((meth)acryloyloxy)ethyl-2'-(triethylammonio)ethylphosphate, 2-((meth)acryloyloxy)ethyl-2'-(tripropylammonio)ethylphosphate, 2-((meth)acryloyloxy)ethyl-2'-(tributylammonio)ethyl phosphate, 2-((meth)acryloyloxy)propyl-2'-(trimethylammonio)-ethylphosphate, 2-((meth)acryloyloxy)butyl-2'-(trimethylammonio)ethylphosphate, 2-((meth)acryloyloxy)pentyl-2'-(trimethylammonio)ethylphosphate, 2-((meth)acryloyloxy)hexyl-2'-(trimethylammonio)ethyl phosphate, 2-(vinyloxy)ethyl-2'-(trimethylammonio)ethylphosphate, 2-(allyloxy)ethyl-2'-(trimethylammonio)ethylphosphate, 2-(vinyloxycarbonyl)ethyl-2'-(trimethylammonio)ethyl phosphate, 2-(allyloxycarbonyl)ethyl-2'-(trimethylammonio)-ethylphosphate, 2-(vinylcarbonylamino)ethyl-2'-(trimethylammonio)ethylphosphate, 2-(allyloxycarbonylamino)ethyl-2'-(trimethylammonio)ethyl phosphate, 2-(butenoyloxy)ethyl-2'-(trimethylammonio)ethylphosphate, and combinations thereof.

Examples of acrylic monomers having 3 to 16 carbon atoms include without limitation C1-C12 alkyl (meth)acrylates, hydroxy-substituted C2-C12 alkyl (meth)acrylates, carboxy-substituted C2-C12 alkyl (meth)acrylates, NH2-substituted C2-C12 alkyl (meth)acrylates, methylamino-substituted C2-C12 alkyl (meth)acrylates, dimethylamino-substituted C2-C12 alkyl (meth)acrylates, ethylamino-substituted C2-C10 alkyl (meth)acrylates, diethylamino-substituted C2-C8 alkyl (meth)acrylates, C2-C12 alkyl (meth)acrylamides, hydroxy-substituted C2-C12 alkyl (meth)acrylamides, carboxy-substituted C2-C12 alkyl (meth)acrylamides, NH2-substituted C2-C12 alkyl (meth) acrylamides, methylamino-substituted C2-C12 alkyl (meth) acrylamides, dimethylamino-substituted C2-C12 alkyl (meth)acrylamides, ethylamino-substituted C2-C10 alkyl (meth)acrylamides, diethylamino-substituted C2-C8 alkyl (meth)acrylamides, ethylene glycol (meth)acrylate, di(ethylene glycol) (meth)acrylate, tri(ethylene glycol) (meth) acrylate, tetra(ethylene glycol) (meth)acrylate, ethylene glycol methyl ether (meth)acrylate, di(ethylene glycol) methyl ether (meth)acrylate, tri(ethylene glycol) methyl ether (meth)acrylate, tetra(ethylene glycol) methyl ether (meth) acrylate, and combinations thereof.

According to the present invention, the ophthalmic composition is substantially free of a borate. Substantially free of a borate refers to be less than 0.1% W/V borate, preferably less than 0.05% W/V borate, more preferably less than 0.02% W/V borate. The borate compounds which may be used in the compositions of the present invention are boric acid and other pharmaceutically acceptable salts such as sodium borate (borax), potassium borate, calcium borate, magnesium borate, manganese borate, and other such borate salts. As used herein, the term "borate" refers to all, pharmaceutically suitable forms of borates. Borates are common excipients in ophthalmic formulations due to good buffering capacity at physiological pH and well known safety and compatibility with a wide range of drugs and preservatives. Borates also have inherent bacteriostatic and fungistatic properties, and therefore aid in the preservation of the compositions.

It is understood that the particular amounts of the galactomannan polymer and the hydrophilic copolymer will vary, depending on the particular gelling properties desired. In general, the concentration of the hydrophilic copolymer or the galactomannan polymer may be manipulated in order to arrive at the appropriate viscosity of the ophthalmic composition upon gel activation (i.e., after administration). If a strongly gelling composition is desired, then the concentration of the hydrophilic copolymer or the galactomannan polymer may be increased. If a weaker gelling composition is desired, such as a partially gelling composition, then the concentration of the hydrophilic copolymer or the galactomannan polymer may be reduced. Other factors may influence the gelling features of the compositions of the present invention, such as the nature and concentration of additional ingredients in the compositions, such as salts, preservatives, chelating agents and so on. Generally, preferred non-gelled compositions of the present invention, i.e., compositions not yet gel-activated by the eye, will have a viscosity of from about 5 to 1000 cps. Generally, preferred gelled compositions of the present invention, i.e., compositions gel-activated by the eye, will have a viscosity of from about 50 to 50,000 cps.

Cross-linking of boronic acids in the hydrophilic copolymer and galactomannan is influenced by factors such as pH, among others, and such cross-linking and the molecular weight of the hydrophilic copolymer in turn influences the viscosity of the solution.

In a preferred embodiment, the ophthalmic compositions of the invention may be formulated at from about 6.5 to about 8.5, preferably from about 7.0 to about 8.0) and require only a minor pH change to activate gelation (i.e., about 0.5 to 1.0 pH unit). Topical formulations (particularly topical ophthalmic formulations, as noted above) are preferred which have a physiological pH matching the tissue to which the formulation will be applied or dispensed.

In another preferred embodiment, the ophthalmic composition of the present invention comprises at least one cis-diol compound at a concentration that inhibits cross-linking of the galactomannan polymer and hydrophilic copolymer. Once instilled in the eye, the cis-diol compound is diluted by the natural tear film allowing a gradual increase in the cross-linking of the galactomannan polymer and hydrophilic copolymer and a corresponding gradual increase in viscosity and elasticity. This gradual increase in viscosity, cross-linking, and elasticity allows for effective spreading and less blurring upon contact, yet provides long lasting lubrication and corneal surface protection. A cis-diol compound is any compound that comprise hydroxyl groups attached to adjacent carbon atoms. Exemplary cis-diol compounds include, but are not limited to, hydrophilic carbohydrates (e.g., sorbitol, mannitol), propylene glycol, glycerol, and combinations thereof. Preferred cis-diol compounds of the present invention include propylene glycol, sorbitol, mannitol and combinations thereof. The cis-diol compounds are present at concentrations of about 0.5 to 5.0 w/v %, preferably about 0.5 to 2.0 w/v % in the compositions of the present invention.

The ophthalmic compositions of the present invention optionally comprise a pharmaceutically acceptable divalent cation salt such as magnesium chloride. Divalent cations such as calcium generally interact with galactomannan and borate to strengthen cross-linking behavior. When present in galactomannan- and borate-containing formulations, divalent cations can increase the overall viscosity of such formulations. Divalent cations include, but are not limited to, magnesium, chloride, and zinc cations. Generally, concentrations of divalent cations should be 0 to 0.25 w/v %.

The ophthalmic compositions of the present invention may optionally comprise one or more additional excipients and/or one or more additional active ingredients. Excipients commonly used in pharmaceutical formulations include, but are not limited to, demulcents, tonicity-adjusting agents, preservatives, chelating agents, buffering agents, and surfactants. Other excipients comprise solubilizing agents, stabilizing agents, comfort-enhancing agents, polymers, emollients, pH-adjusting agents and/or lubricants. Any buffer of a variety of excipients may be used in formulations of the present invention including water, mixtures of water and water-miscible solvents, such as C1-C7-alkanols, vegetable oils or mineral oils comprising from 0.5 to 5% non-toxic water-soluble polymers, natural products, such as alginates, pectins, tragacanth, karaya gum, xanthan gum, carrageenin, agar and acacia, starch derivatives, such as starch acetate and hydroxypropyl starch, and also other synthetic products such as polyvinyl alcohol, polyvinylpyrrolidone, polyvinyl methyl ether, polyethylene oxide, preferably cross-linked polyacrylic acid and mixtures of those products.

Demulcents used with embodiments of the present invention include, but are not limited to, glycerin, polyvinyl pyrrolidone, polyethylene oxide, polyethylene glycol, polyethyleoxide-polybutyleneoxide block copolymer, polyethyleneoxide-polypropyleneoxide block copolymer, propylene glycol, polyacrylic acid, and combinations thereof. Particularly preferred demulcents are propylene glycol and polyethylene glycol 400.

Suitable tonicity-adjusting agents include, but are not limited to, mannitol, sodium chloride, glycerin, and the like. Suitable buffering agents include, but are not limited to, phosphates, acetates and the like, and amino alcohols such as 2-amino-2-methyl-1-propanol (AMP). Suitable surfactants include, but are not limited to, ionic and nonionic surfactants, though nonionic surfactants are preferred, RLM 100, POE 20 cetylstearyl ethers such as Procol® CS20 and poloxamers such as Pluronic® F68, and block copolymers such as poly(oxyethylene)-poly(oxybutylene) compounds set forth in U.S. Pat. Appl. Pub. No. 2008/0138310.

The compositions set forth herein may comprise one or more preservatives. Examples of such preservatives include p-hydroxybenzoic acid ester, sodium perborate, sodium chlorite, alcohols such as chlorobutanol, benzyl alcohol or phenyl ethanol, guanidine derivatives such as polyhexamethylene biguanide, sodium perborate, polyquaternium-1 (aka, POLYQUAD® or ONAMERM®), or sorbic acid. The use of low molecular weight amino alcohols in ophthalmic compositions is described. The compositions set forth herein may comprise low molecular weight amino alcohols (molecular weight of 60 to 200 grams/mole) to enhance the efficacy of anti-microbial preservatives. The amino alcohol is 2-amino-2-methyl-1-propanol (AMP), 2-dimethylaminomethyl-1-propanol (DMAMP), 2-amino-2-ethyl-1,3-propanediol (AEPD), 2-amino-2-methyl-1,3-propanediol (AMPD), 2-amino-1-butanol (AB), or combinations thereof. In certain embodiments, the composition may be self-preserved so that no preservation agent is required.

Compositions of the present invention are ophthalmically suitable for application to a subject's eyes. The term "aqueous" typically denotes an aqueous formulation wherein the excipient is >50%, more preferably >75% and in particular >90% by weight of water. These drops may be delivered from a single dose ampoule which may preferably be sterile and thus render bacteriostatic components of the formulation unnecessary. Alternatively, the drops may be delivered from a multi-dose bottle which may preferably comprise a device which extracts any preservative from the formulation as it is delivered, such devices being known in the art.

The compositions of the present invention are preferably isotonic, or slightly hypotonic in order to combat any hypertonicity of tears caused by evaporation and/or disease. This may require a tonicity agent to bring the osmolality of the formulation to a level at or near 210-320 milliosmoles per kilogram (mOsm/kg). The compositions of the present invention generally have an osmolality in the range of 220-320 mOsm/kg, and preferably have an osmolality in the range of 235-300 mOsm/kg. The ophthalmic compositions will generally be formulated as sterile aqueous solutions.

In another preferred embodiment, an ophthalmic composition of the invention is an aqueous solution.

In another preferred embodiment, an ophthalmic composition of the invention is an emulsion that comprises the hydrophilic copolymer containing phospholipid of the present invention and at least one ophthalmic oil dispersed throughout the continuous water or aqueous phase as small droplets that are substantially distinct and separate. It should be understood that, as used herein, the phase distinct and separate means that, at any give point in time, the droplets are distinct and separate. However, the droplets of the emulsion can combine and separate over time to maintain an average droplet size or diameter. The droplets of the emulsion of the present invention typically have an average or mean diameter no greater than about 1500 nanometers (nm), more typically no greater than about 1000 nm and still more typically no greater than about 600 nm. These droplets also typically have an average or mean diameter that is typically at least 2 nm, more typically at least 10 nm and still more typically at least 100 nm.

Particle or droplet size analyzers may be used to determine emulsion oil droplet size. For example, a Microtrac S3500 Particle Size Analyzer (Software Version 10.3.1) is a tri-laser particle size analyzer that can be used to measure emulsion oil droplet size. That particular analyzer measures laser light diffracted (scattered) from particles (e.g., droplets) in a flowing stream. The intensity and direction of the scattered light is measured by two optical detectors. Mathematical analysis of the diffraction pattern by the software generates a volume distribution of droplet size. The droplet diameter corresponding to 90% of the cumulative undersize distribution by volume is used.

It is believed that phospholipid containing in the hydrophilic copolymer can strengthen and/or stabilize the tear film lipid layer. By having a stabilized lipid layer, water evaporation can be reduced and symptom of dryness of the eye may be alleviated. It is also believed that phospholipids can aid in maintaining the stability of the emulsion and for reducing droplet size of the ophthalmic oil.

Examples of ophthalmic oils include without limitation any of numerous mineral oils, vegetable oil, synthetic substances, and/or animal and vegetable fats or any combination of oils. The oil can be soluble in various organic solvents such as ether but not in water. The oil phase can comprise, if desired, monoglycerides, diglycerides, triglycerides, glycolipids, glyceroglycolipids, sphingolipids, sphingo-glycolipids, fatty alcohols, hydrocarbons having a $C_{12}$-$C_{28}$ chain in length, wax esters, fatty acids, mineral oils, and silicone oils. Mineral oil is particularly preferred. A silicone oil may also be used. The oil phase can additionally include a waxy hydrocarbon, such as paraffin waxes, hydrogenated castor oil, Synchrowax HRC, Carnauba, beeswax, modified beeswaxes, microcrystalline waxes, and polyethylene waxes. The oil is typically at least 0.01 w/v %, more typically at least 0.1 w/v % and even more typically 0.8 w/v % of the emulsion. The oil is also typically no greater than about 20 w/v %, more typically no greater than about 5 w/v % and even more typically no greater than about 3 or even 1.5 w/v % of the emulsion The emulsion will also typically include a hydrophilic surfactant (high HLB) and a hydrophobic (low HLB) surfactant. The emulsions of the present invention are most desirably used for dry eye therapeutics. However, without limitation, it is also contemplated that the emulsions may be used for drug delivery, vitamin delivery, botanical delivery, contact lens wetting and contact lens lubrication.

The emulsion of the present invention also typically incorporates two or more surfactants, which act as emulsifiers aiding in the emulsification of the emulsion. Typically, these surfactants are non-ionic. The concentration of emulsifying surfactant in the emulsion is often selected in the range of from 0.1 to 10% w/v, and in many instances from 0.5 to 5% w/v. It is preferred to select at least one emulsifier/surfactant which is hydrophilic and has an HLB value of at least 8 and often at least 10 (e.g., 10 to 18). It is further preferred to select at least one emulsifier/surfactant which is hydrophobic and has an HLB value of below 8 and particularly from 1 to 6. By employing the two surfactants/emulsifiers together in appropriate ratios, it is readily feasible to attain a weighted average HLB value that promotes the formation of an emulsion. For most emulsions according to the present invention, the average HLB value is chosen in the range of about 6 to 12, and for many from 7 to 11. For example, the HLB values for exemplary surfactants and mineral oil are as follows: hydrophobic surfactant (2.1), hydrophilic surfactant (16.9) and mineral oil (10.5). The hydrophilic surfactant is typically present in the emulsion in an amount that is at least about 0.01 w/v %, more typically at least about 0.08 w/v % and even more typically at least about 0.14 w/v %. The hydrophilic surfactant is typically present in the emulsion in an amount that is no greater than about 1.5 w/v %, more typically no greater than about 0.8 w/v % and even more typically no greater than about 0.44 w/v %.

The hydrophilic surfactant can be a fatty acid, an ester, an ether, an acid or any combination thereof. The hydrophilic surfactant may be ionic or non-ionic, but is preferably non-ionic. Many suitable surfactants/emulsifiers are non-ionic ester or ether emulsifiers comprising a polyoxyalkylene moiety, especially a polyoxyethylene moiety, often containing from about 2 to 80, and especially 5 to 60 oxyethylene units, and/or contain a polyhydroxy compound such as glycerol or sorbitol or other alditols as hydrophilic moiety. The hydrophilic moiety can contain polyoxypropylene. The emulsifiers additionally contain a hydrophobic alkyl, alkenyl or aralkyl moiety, normally containing from about 8 to 50 carbons and particularly from 10 to 30 carbons. Examples of hydrophilic surfactants/emulsifiers include ceteareth-10 to -25, ceteth-10-25, steareth-10-25, and PEG-15-25 stearate or distearate. Other suitable examples include $C_{10}$-$C_{20}$ fatty acid mono, di or tri-glycerides. Further examples include $C_{18}$-$C_{22}$ fatty alcohol ethers of polyethylene oxides (8 to 12 EO). One particularly preferred hydrophilic surfactant is polyoxyethylene-40-stearate, which is sold under the tradename MYRJ-52, which is commercially available from Nikko Chemicals.

The hydrophobic surfactant is typically present in the emulsion in an amount that is at least about 0.01 w/v %, more typically at least about 0.11 w/v % and even more typically at least about 0.16 w/v %. The hydrophobic surfactant is typically present in the emulsion in an amount that is no greater than about 10.0 w/v %, more typically no greater than about 2.0 w/v % and even more typically no greater than about 0.62 w/v %.

The hydrophobic surfactant can be a fatty acid, an ester, an ether, an acid or any combination thereof. The hydrophobic surfactant may be ionic or non-ionic, but is preferably non-ionic. The hydrophobic surfactant will typically include a hydrophobic moiety. The hydrophobic moiety can be either linear or branched and is often saturated, though it can be unsaturated, and is optionally fluorinated. The hydrophobic moiety can comprise a mixture of chain lengths, for example, those deriving from tallow, lard, palm oil sunflower seed oil or soya bean oil. Such non-ionic surfactants can also be derived from a polyhydroxy compound such as glycerol or sorbitol or other alditols. Examples of hydrophobic surfactants include, without limitation, sorbitan fatty acid esters such as sorbitan monoleate, sorbitan monostearate, sorbitan monolaurate, sorbitan monopalmitate, sorbitan monoisostearate, sorbitan trioleate, sorbitan tristearate, sorbitan sesquloleate, sorbitan sesquistearate, combinations thereof or the like. One particularly preferred hydrophobic surfactant is a sorbitan tristearate sold under the tradename SPAN-65, which is commercially available from Croda Worldwide.

The emulsion of the present invention may be formed using a variety of combining and mixing protocol and techniques known to those skilled in the art. According to one preferred embodiment, however, the ingredients are mixed and combined according to a specific protocol. In such protocol, multiple admixtures are formed and those admixtures are combined to form the emulsion. The first admixture is formed by mixing the oil and the surfactants at an elevated temperature to form an oil phase admixture. The second admixture is formed mixing the anionic phospholipid into purified water at an elevated temperature to form a water phase admixture. Thereafter, the oil phase admixture and the water phase admixture are mixed at an elevated temperature and subsequently homogenized using a homogenizer to form an initial emulsion. A third admixture is formed by mixing the galactomannan polymer with water and adjusting pH as needed to form a galactomannan polymer slurry. The galactomannan polymer slurry is then mixed with initial emulsion and form a polymer enhanced emulsion. A fourth admixture is formed by mixing any combination of the following to form a salt solution: borate, polyol, preservative and any other ingredients. The salt solution and the enhanced emulsion are then mixed followed by the addition of a sufficient quantity (Q.S.) of water and pH adjustment.

The compositions of the present invention can also be used to administer pharmaceutically active compounds and pharmaceutically acceptable salts thereof. Such compounds include, but are not limited to, anesthetic drugs, glaucoma therapeutics, pain relievers, anti-hypertensive, neuro-protective, muco-secretagogue, angiostatic, anti-angiogenesis agents, growth factors, immunosuppressant agents, anesthetic drug, anti-infectives, antiviral agents, anti-inflammatory, anti-angiogenesis agents, anti-myopia agents, anti-allergy agents, dopaminergic antagonists, proteins, and anti-microbials.

Examples of glaucoma therapeutics (or anti-glaucoma agent) include without limitation betaxolol, timolol, pilocarpine, levobetaxolol, apraclonidine, brimonidine, carbonic anhydrase inhibitors (e.g., brinzolamide and dorzolamide), and prostaglandins (e.g., travoprost, bimatoprost, and latanoprost).

Examples of anti-infective agents include without limitation ciprofloxacin and tobramycin.

Anti-inflammatory agents include non-steroidal and steroidal anti-inflammatory agents, such as triamcinolone actinide, naproxen, suprofen, diclofenac, ketorolac, nepafenac, rimexolone, tetrahydrocortisol, and dexamethasone.

Examples of antihypertensive agents include without limitation para-amino clonidine (apraclonidine).

Examples of growth factors include without limitation epidermal growth factor (EGF) and vascular endothelial growth factor (VEGF).

Examples of anti-allergy agents include without limitation olopatadine, epinastine, ketotifen, emedastine, cromolyn.

Examples of antiviral agents include without limitation ganciclovir and valganciclovir. Examples of antimyopia agents include without limitation atropine, pirenzepine, and derivatives thereof.

Anti-angiogenesis agents include anecortave acetate (RE-TAANE®) and receptor tyrosine kinase inhibitors (RTKi).

Local anesthetic drugs can generally be divided into two categories based on chemical structure: "amides" and "esters." See Ophthalmic Drug Facts '99, Facts and Comparisons, St. Louis, Mo., (1999), Ch.3. Examples of suitable anesthetic drugs include proparacaine, lidocaine, cocaine, oxybuprocaine, benoxinate, butacaine, mepivacaine, etidocaine, dibucaine, bupivacaine, levobupivacaine, tetracaine and procaine. Most preferred are levobupivacaine, proparacaine and tetracaine.

The ophthalmic compositions of the invention can be particularly useful for delivery therapeutic agents that relieve symptoms of dry eye conditions, cooling agents, antioxidants (omega-3 and omega-6 fatty acids), nutriceuticals (e.g., vitamin A, vitamin D, vitamin E, tocopherols, vitamin K, beta-carotene), and other bioactivities for ophthalmic uses. Generally, amounts of therapeutic agent, when used, can be quite variable depending upon the agent or agents used. As such, the concentration of therapeutic agent can be at least about 0.005 w/v %, more typically at least about 0.01 w/v % and even more typically at least about 0.1 w/v %, but typically no greater than about 10 w/v %, more typically no greater than about 4.0 w/v %, still more typically no greater than about 2.0 w/v %.

Optionally, the compositions of the present invention may be formulated without a pharmaceutically active compound. Such compositions may be used to lubricate the eye or provide artificial tear solutions to treat, for example, dry eye. In general, artificial tear solutions will contain tonicity agents, polymers and preservatives, as described above. The amount of galactomannan and hydrophilic copolymer contained in the artificial tear solutions will vary, as described above, but will generally be in the amount of from 0.1 to 1.0% (w/v) and 0.1 to 4.0% (w/v), respectively.

The compositions of the invention may include additional or alternative polymeric ingredients and/or viscosity agents. Examples include, without limitation, carboxymethylcellulose, hydroxypropylmethyl cellulose, hydroxyethyl cellulose, carboxyvinyl polymer, xanthan gum, hyaluronic acid, any combinations thereof or the like.

In accordance with the invention, a composition of the present invention is administered once a day. However, the compositions may also be formulated for administration at any frequency of administration, including once a week, once every 5 days, once every 3 days, once every 2 days, twice a day, three times a day, four times a day, five times a day, six times a day, eight times a day, every hour, or greater frequency. Such dosing frequency is also maintained for a varying duration of time depending on the therapeutic regimen. The duration of a particular therapeutic regimen may vary from one-time dosing to a regimen that extends for months or years. One of ordinary skill in the art would be familiar with determining a therapeutic regimen for a specific indication.

Although various embodiments of the invention have been described using specific terms, devices, and methods, such description is for illustrative purposes only. The words used are words of description rather than of limitation. It is to be understood that changes and variations may be made by those skilled in the art without departing from the spirit or scope of the present invention, which is set forth in the following claims. In addition, it should be understood that aspects of the various embodiments may be interchanged either in whole or in part or can be combined in any manner and/or used together, as illustrated below:

The previous disclosure will enable one having ordinary skill in the art to practice the invention. Various modifications, variations, and combinations can be made to the various embodiment described herein. In order to better enable the reader to understand specific embodiments and the advantages thereof, reference to the following examples is suggested. It is intended that the specification and examples be considered as exemplary.

Chemicals

The following abbreviations are used in the following examples: NVP represents N-vinylpyrrolidone; VPBA represents 4-vinylphenylboronic acid; PVA represents polyvinylalcohol; MPG represent 2-methacryloyloxyethyl phosphorylcholine; $PEG_{300}MA$ represents polyethylene glycol monomethacrylate having a number average molecular weight, Mn, of 300 Daltons; $PEG_{950}MA$ represents polyethylene glycol monomethacrylate having a number average molecular weight, Mn, of 950 Daltons; DMA represents N,N-dimethylacrylamide; BMA represents n-butyl methacrylate; DGMEMA represents di(ethylene glycol) methacrylate; AAPH (Vazo-56) represent 2,2'-azobis-(2-amidinopropane dihydrochloride; DI water represents deionized water; βME represents β-mercaptoethanol; HPMC represents hydroxypropyl methylcellulose; PEG400 represents polyethylene glycol having a number average molecular weight of 400 Daltons, AMP represent 2-Amino-2-methyl-propanol.

Example 1

Synthesis of Terpolymer-Poly($PEG_{200}$MA-co-MPC-co-VPBA) Terpolymer

About 1.011 g of VPBA is dissolved in 25.0 g PrOH to obtain a VPBA solution which is introduced, through a syringe equipped with a 5 μm nylon filter, into a 500 mL reactor equipped with $N_2$ inlet, overhead stirrer, thermocouple, condenser, and bubbler. About 12.278 g of $PEG_{200}MA$ is dissolved in 20.0 g DI water, poured into the reactor and rinsed in with an additional 15.0 g DI water. About 6.714 g of MPC is dissolved in 20.0 g DI water, poured into the reactor and rinsed in with an additional 15.0 g DI water. About 00693 g of AAPH is dissolved in 5.0 g deionized water, poured into reactor and rinsed in with an additional 2×5.0 g deionized water, followed by 5.0 g deionized water and 65.0 g n-propanol. About 3.65 mL of mercaptoethanol (βME) solution (0.274 g βME in 100 mL of DI water) is added with a micropipette.

The reaction solution is purged with nitrogen (200 mL/minute) for 30 minutes at 20° C. while stirring at 150 rpm. Nitrogen flow is reduced to a blanket and the copolymerization solution is heated according to the following schedule: taking two hours to reach 61° C.; maintaining at 61° C. for about 8 hours; and taking 2 hours to cool down to 20° C.

Various copolymers (binary or ternary) are prepared according to the procedures described above except different amounts and types of vinylic monomers as indicated in Table 1.

TABLE 1

| | Component (mole %) | | | | [BA]* | Mn | Mw | |
|---|---|---|---|---|---|---|---|---|
| | VPBA | $PEG3_{300}MA$ | $PEG_{950}MA$ | $PEG_{200}MA$ | MPC | (meq/g) | (KD) | (KD) | PDI |
| Terpolymer 1 | 7.5 | 67.5 | 0 | 0 | 25.0 | 0.22 | 181 | 328 | 1.8 |
| Terpolymer 2 | 7.5 | 0 | 67.5 | 0 | 25.0 | 0.10 | 152 | 398 | 2.6 |
| Terpolymer 3 | 7.5 | 0 | 0 | 67.5 | 25.0 | 0.32 | 74 | 122 | 1.6 |
| Terpolymer 4 | 12.5 | 0 | 0 | 62.5 | 25.0 | 0.51 | 142 | 229 | 1.6 |

*the concentration (milliequivalents) of boronic acid (BA) groups in a copolymer is determined by titration Example 2

Synthesis of Ternary Copolymers
Poly($MPC_{0.4}$-co-$NVP_{0.5}$-co-$VPBA_{0.1}$)

In a 20 ml vial, add 1.18 g (4 mmol) of MPC, 0.556 g (5 mmol) of NVP and 0.148 g (1 mmol) of VPBA and 10 ml Ethanol, vazo64 1.64 mg (0.01 mmol) are added. Nitrogen gas is gently bubbled into the solution for 5 min to eliminate the oxygen and then the vial is sealed. The polymerization is performed at 60° C. for a 6 hrs. After cooling the vial, the contents are poured into a large amount of a mixture of diethyl ether and chloroform (8/2 by volume) to eliminate any remaining monomer and precipitate the polymer. The precipitate is filtered off using a glass-filter and dried in vacuum.

Poly($MPC_{0.6}$-co-$BMA_{0.3}$-co-$VPBA_{0.1}$)

In a 20 ml vial, add 1.77 g (6 mmol) of MPC, 0.426 g (3 mmol) of BMA and 0.148 g (1 mmol) of VPBA and 10 ml Ethanol, vazo64 1.64 mg (0.01 mmol) are added. Nitrogen gas is gently bubbled into the solution for 5 min to eliminate the oxygen and then the vial is sealed. The polymerization is performed at 60° C. for a 6 hrs. After cooling the vial, the contents are poured into a large amount of a mixture of diethyl ether and chloroform (8/2 by volume) to eliminate any remaining monomer and precipitate the polymer. The precipitate is filtered off using a glass-filter and dried in vacuum. The obtained copolymer is determined to have a weight average molecular weight, Mw, of 150 KDa.

Poly($MPC_{0.8}$-co-$BMA_{0.1}$-co-$VPBA_{0.1}$)

In a 20 ml vial, add 2.36 g (8 mmol) of MPC, 0.142 g (1 mmol) of BMA and 0.148 g (1 mmol) of VPBA and 10 ml Ethanol, vazo64 1.64 mg (0.01 mmol) are added. Nitrogen gas is gently bubbled into the solution for 5 min to eliminate the oxygen and then the vial is sealed. The polymerization was performed at 60° C. for a 6 hrs. After cooling the vial, the contents are poured into a large amount of a mixture of diethyl ether and chloroform (8/2 by volume) to eliminate any remaining monomer and precipitate the polymer. The precipitate is filtered off using a glass-filter and dried in vacuum. The obtained copolymer is determined to have a weight average molecular weight, Mw, of 160 KDa. Poly(MPC$_{0.8}$-co-BMA$_{0.1}$-co-VPBA$_{01}$)

In a 40 ml vial, add 4.72 g (16 mmol) of MPC, 0.285 g (2 mmol) of BMA and 0.296 g (2 mmol) of VPBA and 20 ml Ethanol, vazo64 3.2 mg (0.02 mmol) are added. Nitrogen gas is gently bubbled into the solution for 5 min to eliminate the oxygen and then the vial is sealed. The polymerization is performed at 60° C. for a 6 hrs. After cooling the vial, the contents are poured into a large amount of a mixture of diethyl ether and chloroform (8/2 by volume) to eliminate any remaining monomer and precipitate the polymer. The precipitate is filtered off using a glass-filter and dried in vacuum. The obtained copolymer is determined to have a weight average molecular weight, Mw, of 286 KDa. Poly(MPC$_{0.8}$-co-BMA$_{0.1}$-co-VPBA$_{0.1}$)

In a 40 ml vial, add 4.72 g (16 mmol) of MPC, 0.285 g (2 mmol) of BMA and 0.296 g (2 mmol) of VPBA and 20 ml Ethanol, vazo64 1.3 mg (0.01 mmol) are added. Nitrogen gas is gently bubbled into the solution for 5 min to eliminate the oxygen and then the vial is sealed. The polymerization is performed at 60° C. for a 6 hrs. After cooling the vial, the contents are poured into a large amount of a mixture of diethyl ether and chloroform (8/2 by volume) to eliminate any remaining monomer and precipitate the polymer. The precipitate is filtered off using a glass-filter and dried in vacuum. The obtained copolymer is determined to have a weight average molecular weight, Mw, of 386 KDa. Poly(MPC$_{0.8}$-co-BMA$_{0.1}$-co-VPBA$_{0.1}$), In a 40 ml vial, add 4.72 g (16 mmol) of MPC, 0.285 g (2 mmol) of BMA and 0.296 g (2 mmol) of VPBA and 10 ml Ethanol, vazo64 3.2 mg (0.02 mmol) are added. Nitrogen gas is gently bubbled into the solution for 5 min to eliminate the oxygen and then the vial is sealed. The polymerization is performed at 60° C. for a 6 hrs. After cooling the vial, the contents are poured into a large amount of a mixture of diethyl ether and chloroform (8/2 by volume) to eliminate any remaining monomer and precipitate the polymer. The precipitate is filtered off using a glass-filter and dried in vacuum. The obtained copolymer is determined to have a weight average molecular weight, Mw, of 688 KDa.

Example 3

Synthesis of Ternary Copolymers

Add 2-methacryloyloxyethyl phosphorylcholine (MPC) (Mw=295.27), 4-vinyl phenyl boronic acid (VPBA, Mw=147.97), and optionally a third monomer (n-butyl methacrylate (BMA, Mw=142.20) or di(ethylene glycol) methyl ether methacrylate (DGMEMA, Mw=188.22), ethanol, and DI water into a 1 L jacketed reactor, in the amounts shown in Table 8. Degas the solution for 30 minutes at a nitrogen flow rate of 250 ml/min. Dissolve Vazo-56 into 20 to 30 g of DI water. Degas the initiator solution for 30 minutes at a nitrogen flow rate of about 50 mL/min. in an addition funnel. Heat the solution in the reactor to 49° C. Add initiator solution and maintain solution temperature for 16 hours.

Purification:

Dilute solution after the reaction to about 10% solids with DI water. Filter solution from synthesis step through a course-fritted filter. Dilute solution to 7.5-5.0% solids for purification by ultrafiltration using a polyether sulfone membrane with 30 kDa molecular weight cutoff. Use 8 to 10 bed volumes of water to remove residual monomer and solvent.

Polymer Characterization:

The boronic acid content of the copolymer is determined by carrying an acid base titration in the presence of mannitol. The results are reported in Table 2.

The weight average molecular weight of the copolymers are determined using GPC with an RI detector and PEG standards. The results are reported in Table 2.

TABLE 2

| Components | Synthesis | | |
| --- | --- | --- | --- |
|  | Copolymer 9A | Copolymer 9B | Copolymer 9C |
| MPC (g) | 66.80 | 59.03 | 158.21 |
| VPBA (g) | 4.187 | 3.696 | 9.908 |
| BMA (g) | 4.023 | — | — |
| DGMEMA (g) | — | 4.702 | 12.606 |
| Vazo-56 (g) | 0.0768 | 0.0679 | 0.1818 |
| Ethanol (g) | 212.5 | 191 | 257.1 |
| Water (g) | 212.5 | 191 | 257.1 |
| Mw (kDa) | 993 | 579 | 2.176 |
| Mn (kDa) | 317 | 148 | 460 |
| PDI (Mw/Mn) | 3.1 | 4.0 | 4.7 |
| Boronic acid (meq/g) | 0.341 | 0.495 | 0.325 |

Example 4

Ophthalmic Compositions

The solutions of control 1, Control 2 and Expt 2 are prepared as composition (% w/w) listed below (Table 3). The proposal amount ingredients as % w/w are weighed in a glass bottle. The solution is stirred at room temperature till full dissolution. Filtration is conducted by a 5 μm filter. The solution go to be autoclaved at 121° C. for 45 min. The pH value of each solution is measured via a normal pH meter.

TABLE 3

|  | Control 1 (% W/W) | Control 2 (% W/W) | Expt. 2 (% W/W) |
| --- | --- | --- | --- |
| HP GUAR (HP8A) | 0.17 | 0.17 | 0.17 |
| PEG 400 | 0.4 | 0.4 | 0.4 |
| Propylene Glycol | 0.3 | 0.3 | 0.3 |
| Boric Acid | 0 | 0.7 | 0 |
| Hydrophilic Copolymer | 0 | 0 | 0.7* |
| Potassium Chloride | 0.12 | 0.12 | 0.12 |
| Sodium Chloride | 0.1 | 0.1 | 0.1 |
| Sorbitol | 1.4 | 1.4 | 1.4 |
| 2-Amino-2-methylpropanol (AMP) | 0.57 | 0.57 | 0.57 |
| Purified Water | QS | QS | QS |
| Adjusted PH | 7.9 | 7.9 | 7.9 |

Hydrophilic Copolymer in Expt. 2 is a copolymer of 7.5% mole VPBA, 67.5% mole PEG300MA and 25% mole MPC
Viscosity vs. Shear Rate:

To investigate the solution viscosity at high shear rate (4000 s-1), the solutions' pH of C1 and E2 are adjusted to pH 7.9 with 0.1 N HCl (aq.). Solutions' viscosities are conducted at RheoSense microVISC Portable Viscometer. The operation mode is set as Advanced with a shear rate at $100S^{-1}$, $1000 S^{-1}$ and $4000 S^{-1}$, respectively. The measure temperature is set at 34° C. At 4000 s-1 shear rate, the E2 showed higher viscosity than C2. This results as shown in below Table 4 demonstrate that when a drop is in the bottle or instilled through the bottle and subjected at a lower shear rate, for example $100 S^{-1}$, the present formulation has a lower viscosity (10.59 vs. 15.99) than the control 2 formulation. Therefore, it is easier to instill the drop of the present formulation. However, once the drop has been instilled on the eye and the eyelids spread the drop fluid over the eye, the rate of shear during blinking is much high shear rate, for example at $4000 S^{-1}$, the present formulation has a slighter higher viscosity (4.55 vs 4.42) than the control 2 formulation. Therefore, the drop of the present formulation may stay on the eye longer and yield prolonged ocular comfort.

TABLE 4

|  | Control 1 (% W/W) | Control 2 (% W/W) | Expt. 2 (% W/W) |
| --- | --- | --- | --- |
| Viscosity at shear rate at 100 s$^{-1}$ | 10.95 | 15.89 | 10.59 |
| Viscosity at shear rate at 1000 s$^{-1}$ | 6.52 | 9.75 | 6.51 |
| Viscosity at shear rate at 4000 s$^{-1}$ | 4.13 | 4.42 | 4.65 |

What is claimed is:

1. An ophthalmic composition, comprising: from about 0.05 w/v % to about 5 w/v % of galactomannan polymer; a cis-diol and about 0.5 w/v % to about 10 w/v % of a hydrophilic copolymer which comprises (a) arylborono-containing repeating units each having a boronic acid, (b) repeating units of at least one phosphorylcholine-containing vinylic monomer, and (c) acrylic monomeric units of at least one acrylic monomer having 3 to 16 carbon atoms, the composition is substantially free of a borate.

2. The ophthalmic composition of claim 1, wherein said at least one arylborono-containing vinylic monomer is a vinylic monomer of formula (II) in which:

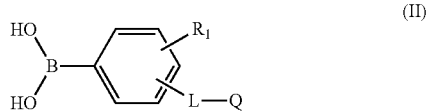

(II)

$R_1$ is H, $NO_2$, F, Cl, or $CF_3$; Q is a monovalent radical of

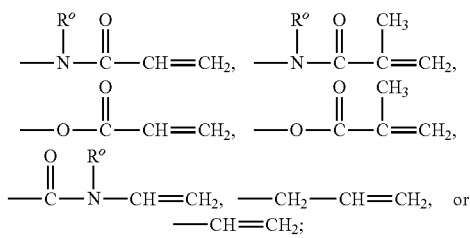

L is a direct bond, a $C_1$-$C_4$ alkylene divalent radical, a divalent radical of

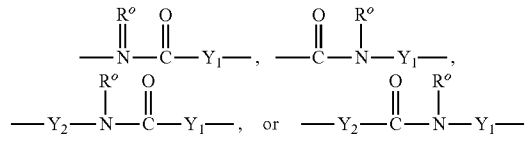

in which $Y_1$ is CH(OH) or a $C_1$-$C_4$ alkylene divalent radical, $Y_2$ is a $C_1$-$C_4$ alkylene divalent radical, and $R^o$ is H or a $C_1$-$C_4$ alkyl.

3. The ophthalmic composition of claim 2, wherein said at least one arylborono- containing vinylic monomer is selected from the group consisting of 3-vinylphenylboronic acid, 4-vinylboronic acid, 3-(meth)acrylamidophenylboronic acid, 4-(meth)acrylamidophenylboronic acid, and combinations thereof.

4. The ophthalmic composition of claim 1, wherein the phosphorylcholine-containing vinylic monomer is selected from the group consisting of (meth)acryloyloxyethyl phosphorylcholine, (meth)acryloyloxypropyl phosphorylcholine, 4-((meth)acryloyloxy)butyl-2'-(trimethylammonio)ethylphosphate, 2-[(meth)acryloylamino]ethyl-2'-(trimethylammonio)-ethylphosphate, 3-[(meth)acryloylamino]propyl-2'-(trimethylammonio)ethylphosphate, 4-[(meth)acryloylamino]butyl-2'-(trimethylammonio)ethylphosphate, 5-((meth)acryloyloxy)pentyl-2'-(trimethylammonio)ethyl phosphate, 6-((meth)acryloyloxy)hexyl-2'-(trimethylammonio)-ethylphosphate, 2-((meth)acryloyloxy)ethyl-2'-(triethylammonio)ethylphosphate, 2-((meth)acryloyloxy)ethyl-2'-(tripropylammonio)ethylphosphate, 2-((meth)acryloyloxy)ethyl-2'-(tri butylammonio)ethyl phosphate, 2-((meth)acryloyloxy)propyl-2'-(trimethylammonio)-ethylphosphate, 2-((meth)acryloyloxy)butyl-2'-(trimethylammonio)ethylphosphate, 2-((meth)acryloyloxy)pentyl-2'-(trimethylammonio)ethylphosphate, 2-((meth)acryloyloxy)hexyl-2'-(trimethylammonio)ethyl phosphate, 2-(vinyloxy)ethyl-2'-(trimethylammonio)ethylphosphate, 2-(allyloxy)ethyl-2'-(trimethylammonio)ethylphosphate, 2-(vinyloxycarbonyl)ethyl-2'-(trimethylammonio)ethyl phosphate, 2-(allyloxycarbonyl)ethyl-2'-(trimethylammonio)-ethylphosphate, 2-(vinylcarbonylamino)ethyl-2'-(trimethylammonio)ethylphosphate, 2-(allyloxycarbonylamino)ethyl-2'-(trimethylammonio)ethyl phosphate, 2-(butenoyloxy)ethyl-2'-(trimethylammonio)ethylphosphate, and combinations thereof.

5. The ophthalmic composition of claim 1, wherein said at least one at least one acrylic monomer is selected from the group consisting of a C1-C12 alkyl (meth)acrylate, a hydroxy-substituted C2-C12 alkyl (meth)acrylate, a carboxy-substituted C2-C12 alkyl (meth)acrylate, an NH2-substituted C2-C12 alkyl (meth)acrylate, a methylamino-substituted C2-C12 alkyl (meth)acrylate, a dimethylamino-substituted C2-C12 alkyl (meth)acrylate, an ethylamino-substituted C2-C10 alkyl (meth)acrylate, a diethylamino-substituted C2-C8 alkyl (meth)acrylate, a C2-C12 alkyl (meth)acrylamide, a hydroxy-substituted C2-C12 alkyl (meth)acrylamide, a carboxy-substituted C2-C12 alkyl (meth)acrylaide, an NH2-substituted C2-C12 alkyl (meth)acrylamide, a methylamino-substituted C2-C12 alkyl (meth)acrylamide, a dimethylamino-substituted C2-C12 alkyl (meth)acrylamide, an ethylamino-substituted C2-C10 alkyl (meth)acrylamide, a diethylamino-substituted C2-C8 alkyl (meth)acrylamide, ethylene glycol (meth)acrylate, di(ethylene glycol) (meth)acrylate, tri(ethylene glycol) (meth)acrylate, tetra(ethylene glycol) (meth)acrylate, ethylene glycol methyl ether (meth)acrylate, di(ethylene glycol) methyl ether (meth)acrylate, tri(ethylene glycol) methyl ether (meth)acrylate, tetra(ethylene glycol) methyl ether (meth) acrylate, and combinations thereof. (meth)acrylamide, N,N-dimethyl (meth)acrylamide, N-vinylpyrroli-done (NVP), N-vinyl formamide, N-vinyl acetamide, N-vinyl isopropylamide, N-vinyl-N-methyl acetamide, N,N-dimethylaminoethyl (meth)acrylate, N,N-dimethylaminopropyl (meth) acrylamide, N-2-hydroxylethyl (meth)acrylamide, N,N-bis (hydroxyethyl) (meth)acrylamide, N-3-hydroxypropyl (meth)acrylamide, N-2-hydroxypropyl (meth)acrylamide, N-2,3-dihydroxypropyl (meth)acrylamide, N-tris(hydroxymethyl)methyl (meth)acrylamide, 2-hydroxyethyl (meth)acrylate, 3-hydroxypropyl (meth)acrylate, 2-hydroxypropyl (meth)acrylate, glycerol methacrylate (GMA), di(ethylene glycol) (meth)acrylate, tri(ethylene glycol) (meth)acrylate, tetra(ethylene glycol) (meth)acrylate, poly (ethylene glycol) (meth)acrylate having a number average molecular weight of up to 1500, poly(ethylene glycol)ethyl (meth)acrylamide having a number average molecular weight of up to 1500, N-methyl-3-methylene-2-pyrrolidone, 1-ethyl-3-methylene-2-pyrrolidone, 1-methyl-5-methylene-2-pyrrolidone, 1-ethyl-5-methylene-2-pyrrolidone, 5-methyl-3-methylene-2-pyrrolidone, 5-ethyl-3-methylene-2-pyrrolidone, ethylene glycol methyl ether (meth)acrylate, di(ethylene glycol) methyl ether (meth)acrylate, tri(ethylene glycol) methyl ether (meth)acrylate, tetra(ethylene glycol) methyl ether (meth)acrylate, C1-C4-alkoxy poly(ethylene glycol) (meth)acrylate having a weight average molecular weight of up to 1500, methoxy-poly(ethylene glycol)ethyl (meth)acrylamide having a number average molecular weight of up to 1500, allyl alcohol, vinyl alcohol, and combinations thereof.

6. The ophthalmic composition of claim 1, wherein the hydrophilic copolymer comprises (a) from about 1% to about 20% by mole of the arylborono-containing repeating units, (b) from about 60% to about 98% by mole of repeating units of at least one phosphorylcholine-containing vinylic monomer, and (c) from about 1% by mole to about 20% by mole of acrylic monomeric units of at least one acrylic monomer having 3 to 16 carbon atoms, provided that the sum of the mole percentages of components (a), (b) and (c) and other components not listed above is 100%.

7. The ophthalmic composition according to claim 1, wherein the phosphate-modified galactomannan polymer is present in the ophthalmic composition at a concentration of from about 0.05 to about 3 w/v %.

8. The ophthalmic composition according to claim 1, wherein the phosphate-modified galactomannan polymer is present in the ophthalmic composition at a concentration of from about 0.1 to about 1.0 w/v %.

9. The ophthalmic composition according to claim 1, wherein the phosphate-modified galactomannan polymer is present in the ophthalmic composition at a concentration of from about 0.15 to about 0.25 w/v %.

10. The ophthalmic composition of claim 1, wherein the composition has a pH value between 6.5 to 8.5.

11. The ophthalmic composition of claim 1, wherein the ophthalmic composition comprises at least one cis-diol compound at a concentration that reduces (inhibits) cross-linking of the galactomannan polymer by the hydrophilic copolymer.

12. The ophthalmic composition of claim 11, wherein the cis-diol compound is present at a concentration of from about 0.5 to about 5.0 w/v %.

13. The ophthalmic composition according to claim 11, wherein the cis-diol compound is sorbitol, mannitol, propylene glycol, or combinations thereof.

14. The ophthalmic composition according to claim 1, wherein the ophthalmic composition comprises at least one demulcent selected from the group consisting of glycerin, polyvinyl pyrrolidone, polyethylene oxide, polyethylene glycol, polyethyleoxide-polybutyleneoxide block copolymer, polyethyleneoxide-polypropyleneoxide block copolymer, propylene glycol, polyacrylic acid, and combinations thereof.

15. The ophthalmic composition of claim 14, wherein said at least one demulcent demulcent is propylene glycol and polyethylene glycol 400.

16. The ophthalmic composition according to claim 1, wherein the ophthalmic composition comprises an anesthetic drug, a glaucoma therapeutics, a pain reliever, an anti-hypertensive agent, a neuro-protective agent, muco-secretagogue, an angiostatic agent, an anti-angiogenesis agent, a growth factor, an immunosuppressant agent, an anesthetic drug, an anti-infective agent, an antiviral agent, an anti-inflammatory agent, an anti-angiogenesis agent, an anti-myopia agent, an anti-allergy agent, a dopaminergic antagonist, a protein, an anti-microbial, or combinations.

17. The ophthalmic composition according to claim 1, wherein the ophthalmic composition comprises a cooling agent, an antioxidant, a nutriceutical, or combinations thereof.

18. The ophthalmic composition according to claim 1, wherein the ophthalmic composition comprises omega-3 fatty acid, omega-6 fatty acid, vitamin A, vitamin D, vitamin E, tocopherols, vitamin K, beta-carotene, or combinations thereof.

19. The ophthalmic composition according to claim 1, wherein the ophthalmic composition comprises less than 0.1% W/V of borate.

* * * * *